United States Patent [19]

Picha et al.

[11] Patent Number: 5,037,428
[45] Date of Patent: Aug. 6, 1991

[54] VESSEL APPROXIMATION AND ALIGNMENT DEVICE

[75] Inventors: George J. Picha, Independence; Dean J. Secrest, Euclid, both of Ohio

[73] Assignee: Applied Medical Technology, Inc., Independence, Ohio

[21] Appl. No.: 541,534

[22] Filed: Jun. 21, 1990

[51] Int. Cl.$^5$ .............................................. A61B 17/00
[52] U.S. Cl. .................................. 606/155; 606/153; 606/150; 606/148
[58] Field of Search ................. 606/153, 155, 148–150

[56] References Cited

FOREIGN PATENT DOCUMENTS

| 0735244 | 6/1980 | U.S.S.R. | 606/153 |
| 1169631 | 7/1985 | U.S.S.R. | 606/153 |
| 8804539 | 6/1988 | World Int. Prop. O. | 606/155 |

Primary Examiner—David J. Isabella
Assistant Examiner—Elizabeth M. Burke
Attorney, Agent, or Firm—Pearne, Gordon, McCoy & Granger

[57] ABSTRACT

A vessel approximator for use in anastomosis has a pair of opposed arms, each adapted to fit within the end of a vessel segment to be anastomosed. The tips of the arms are tapered to assist in placing an end of a vessel segment onto the arm. A stem extends from the junction of the arms to form a T shape. The stem is substantially thinner than the arms to permit the ends of the vessel segments placed over the arms to be proximate to each other to be sutured together. A ring on the end of the stem allows the device to be sutered in place in the surgical field. A notch at the junction of the arms opposite the stem permits the arms to collapse together when the device is removed from the vessel segments by pulling on the stem.

10 Claims, 2 Drawing Sheets

VESSEL APPROXIMATION AND ALIGNMENT DEVICE

BACKGROUND OF THE INVENTION

1. Field of the Invention

This invention relates to microsurgery and vascular surgery, and more particularly to a device for use in vessel anastomosis that facilitates vessel approximation and alignment.

2. Description of the Prior Art

In vessel anastomosis, it is necessary to bring the vessel segments to be anastomosed into proximity with each other and to stably maintain the ends of the vessel segments in proper position and alignment so that sutures can be placed. There are no known devices suitable for use in microsurgery that will maintain the vessel segments in the proper position for suturing and that can be easily removed after the sutures are in place.

There are various devices shown in the prior art that could be used as vessel approximators, but each of these devices has serious deficiencies. Among these prior art devices are those shown in the following patents: U.S. Pat. No. 4,483,339, issued to Gillis; U.S. Pat. No. 4,587,969, issued to Gillis; U.S. Pat. No. 4,690,684, issued to McGreevy et al.; U.S. Pat. No. 4,744,364, issued to Kensey; U.S. Pat. No. 4,770,176, issued to McGreevy et al.

One of the problems associated with the design of a suitable vessel approximator is providing means for removing the approximator from the vessels after the vessel segments have been, at least partially, sutured together.

To assist in removal of the approximator, the approximator could be made generally T-shaped so that the ends of the vessel segments can be placed on opposed axially extending portions of the device, and the device can be removed by pulling on the other laterally extending portion of the device. Various T-shaped devices are known for diverse medical uses.

For example, U.S. Pat. No. 3,835,863, issued to Goldberg et al., shows a T-shaped tubular device for insertion into an internal duct for drainage. The drainage device has two laterally extending tubes adapted for insertion in a duct, and a base tube that is used in draining fluid from the duct. The device has a notch formed in the head of the T to facilitate collapse of the two tubes during removal of the device from the duct. This device would not be suitable for anastomosis because the tubes inserted in the duct could not serve the alignment function and because it would be difficult to maintain the device in a stable position in the surgical field during the procedure and because it would be difficult to remove.

Canadian Patent No. 666,090, issued to Sierra Engineering, shows a drainage device similar to that of Goldberg et al. Another T-shaped drainage device is shown in U.S. Pat. No. 4,142,528, issued to Whelan et al.

U.S. Pat. No. 4,230,119, issued to Blum, shows a T-shaped micro-hemostat adapted to be inserted through a slit formed in a vessel. The head of the T has two bars which extend in opposite directions within the vessel. On the end of each bar is a cuff that can be inflated to occlude the vessel.

U.S. Pat. No. 4,168,708, issued to Lepley, shows another T-shaped blood vessel occluder which is used in a manner similar to the device shown in the Blum patent.

In these prior art references, the T-shaped device is usually adapted for insertion into a vessel or duct through a slit. None of the devices are designed for use as an approximation and alignment device in which the ends of the vessel segments would be attached to the device so that the vessel segment ends can be stabilized and positioned for suturing. As such, the devices lack the necessary rigidity and suitability for this purpose. In addition, since none of the prior art devices are adapted for use as an approximation device, none of the prior art devices include means for stabilizing the device and maintaining it in position in the surgical field. Furthermore, many of these devices are not readily adapted for removal from the vessels after the sutures are at least partially in place.

SUMMARY OF THE INVENTION

The disadvantages of the prior art clamping devices are overcome by the present invention of a vessel approximation and alignment device which provides for accurate anatomical alignment of the vessel segments during anastomosis and similar procedures. Using the vessel approximation device of the present invention, consistent alignment of vessel segment ends can be achieved during anastomosis.

The vessel approximation device of the present invention provides a pair of opposed arms upon which the ends of the vessel segments can be placed. With the arms of the device inserted into the ends of the vessel segments, collapse of the vessels is prevented when attempting to join the ends together. This maintains the vessels in an expanded condition, providing rapid and efficient vessel approximation and providing assistance in suture placement. The tips of the arms are also tapered to ease positioning of the ends of the vessel segments over the arms.

The vessel approximation device of the present invention is provided with means for suturing the device to the field so that the device will be stabilized and can be maintained in the desired position in the field throughout the period of its use, preventing undesirable movement of the device which would otherwise hamper or impede the vessel approximation.

The present invention provides a surgical device which is brightly colored so that it can be easily and quickly perceived and identified in the field. The device's bright color also assists in the placement of the vessel segments onto the device and provides a visual reference when placing sutures in the vessels.

The device of the present invention provides further assistance in suturing the ends of the vessel segments together by providing a form to support each of the vessel segments. With the vessel supported on the arms of the device during suturing, the device helps to avoid catching the opposite wall of the vessel with a suture which could result in occlusion of the vessel.

The arms of the device also serve to occlude the vessel segments while the alignment and anastomosis is taking place.

These and other advantages are provided by the present invention of a vessel approximation device which comprises a pair of opposed arms, each arm adapted to fit within the end of a vessel segment. The tip of each arm is tapered to assist in placing an end of a vessel segment onto the arm. The device also comprises a stem extending from the junction of the arms to form a T shape. The stem is substantially thinner than the arms to permit the ends of the vessel segments placed over the arms to be proximate to each other to be sutured together. The device also comprises suture attachment means on the end of the stem for suturing the device in place in the surgical field. A notch is located at the junction of the arms opposite the stem to permit the arms to collapse together when the device is removed from the vessel segments by pulling on the stem.

In accordance with another aspect of the present invention, a method of performing vessel anastomosis is provided. One end of a first vessel segment is inserted onto an arm of a T-shaped device having two opposed arms and a stem extending therefrom. One end of a second vessel segment is inserted onto the other arm of the generally T-shaped device. The first and second vessel segments are sutured together except along the side that the stem extends from the arms. The side which has not been sutured forms an opening through which the stem extends. The device is withdrawn through the opening by pulling on the stem, and the opening is sutured closed.

DETAILED DESCRIPTION OF THE PREFERRED EMBODIMENTS

Figure 1:
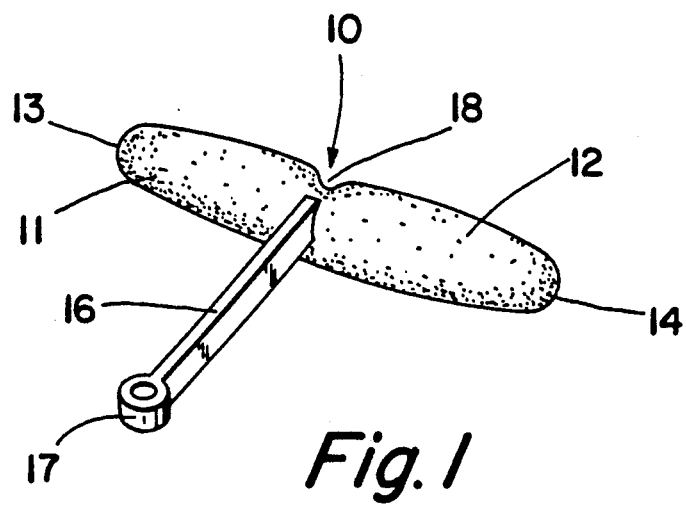
FIG. 1 is a perspective view of the vessel approximation device of the present invention.

Referring more particularly to the drawings and initially to FIG. 1, there is shown one embodiment of the vessel approximation and alignment device 10 of the present invention. The vessel approximation device 10 is generally T-shaped with the top of the T formed by two oppositely extending arms 11 and 12. Each of the arms 11 and 12 is circular in cross section and is adapted to fit inside one end of a vessel segment to be anastomosed. The size of the arms 11 and 12 depends upon the size of the vessels and the size of the field. Preferably, vessel approximation devices in accordance with the present invention would be provided in a variety of sizes for use in various applications. Typical external diameters for the arms 11 and 12 may be 1.0 mm to 4.0 mm, with devices being provided with arms in sizes therebetween in increments of 0.5 mm. The length of each of the arms 11 and 12 depends upon the size of the field, but the arms should be long enough to provide for secure positioning of the vessel segments. The tip 13 or 14 of each arm 11 or 12 is tapered to assist in insertion of the arm into the end of the vessel segment.

Figure 2:
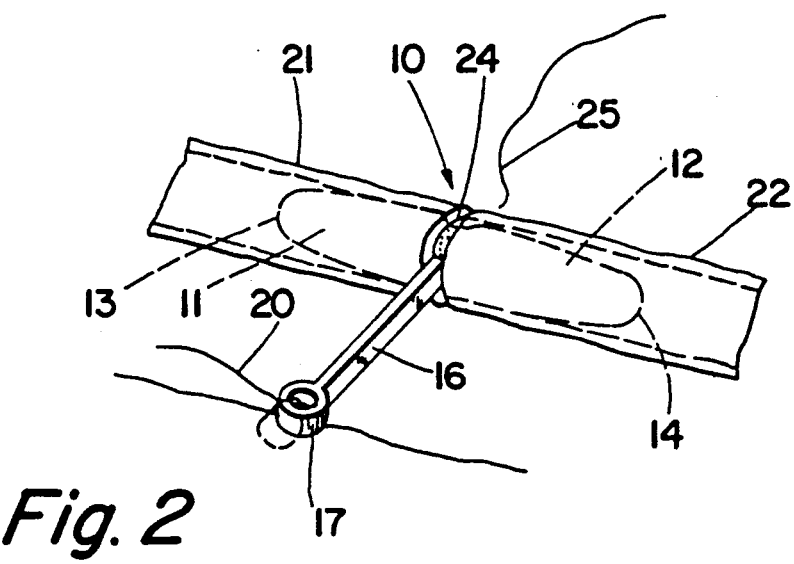
FIG. 2 is a perspective view of the vessel approximation device of FIG. 1 in use in anastomosis.

Extending laterally from the junction of the arms 11 and 12 is a thin pull tab or stem 16. At the end of the stem 16 is a circular ring 17. The ring 17 is preferably in the same plane as the arms 11 and 12. As shown in FIG. 2, the ring 17 is used to allow the vessel approximation device 10 to be sutured to the field to stabilize the device with respect to the vessels while anastomosis is being performed.

At the junction of the arms 11 and 12 opposite the connection of the stem 16 is a notch 18 for assistance in removal of the approximation device 10 from the vessel as will be described below.

The entire vessel approximation device 10 including the arms 11 and 12, the stem 16 and the ring 17 is made of a single injection molded piece made from silicone or other suitable material. The vessel approximation device 10 is preferably colored bright blue or some other contrasting color so that it can be easily identified in the field. As previously mentioned, vessel approximation devices may be provided in a variety of arm sizes depending upon the size of the vessels, and the vessel approximation devices may be color coded to provide an easy indication of their sizes. For example, vessel approximation devices having arms with a diameter of 1.0 mm or 1.5 mm may be colored yellow, vessel approximation devices having arms with a diameter of 2.0 mm or 2.5 mm may be colored green, vessel approximation devices having arms with a diameter of 3.0 mm or 3.5 mm may be colored blue, and vessel approximation devices having arms with a diameter of 4.0 mm or larger may be colored white.

Figure 3:
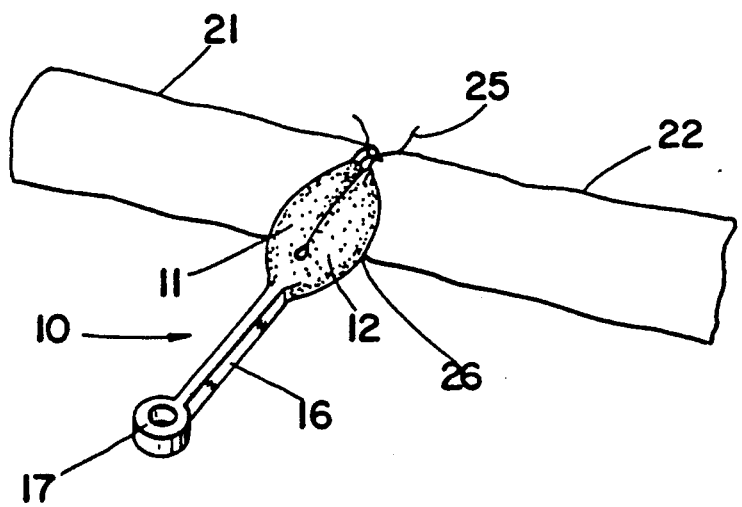
FIG. 3 is a perspective view of the vessel approximation device of FIG. 2 during removal from the vessels.

The use of the vessel approximation device 10 of the present invention can be described more fully with reference to FIGS. 2 and 3.

The location of the anastomosis is noted in the field, and the vessel approximation device 10 of the proper size is selected by measuring the diameter of the vessel segments and selecting a vessel approximation device having a diameter approximately 0.5 mm smaller than the diameter of the vessel segments. The device 10 is positioned and secured in the desired location by placing sutures 20 through the ring 17. The vessel segments 21 and 22 are then repositioned, and the ends of the vessel segments are placed onto the tips 13 and 14 of the arms 11 and 12. As previously noted, the tips 13 and 14 of the arms 11 and 12 are tapered to assist in placing the ends of the vessel segments on the arms.

After the ends of the vessel segments 21 and 22 have been placed onto the arms 11 and 12, the vessel segments have then been properly positioned with respect to each other and properly aligned. However, the ends of the vessel segments 21 and 22 are not yet completely in contact with each other because the thickness of the stem 16 requires that there be a small gap 24 (FIG. 2) between the ends of the vessel segments. For this reason, the stem 16 should be as thin as possible.

Figure 4:
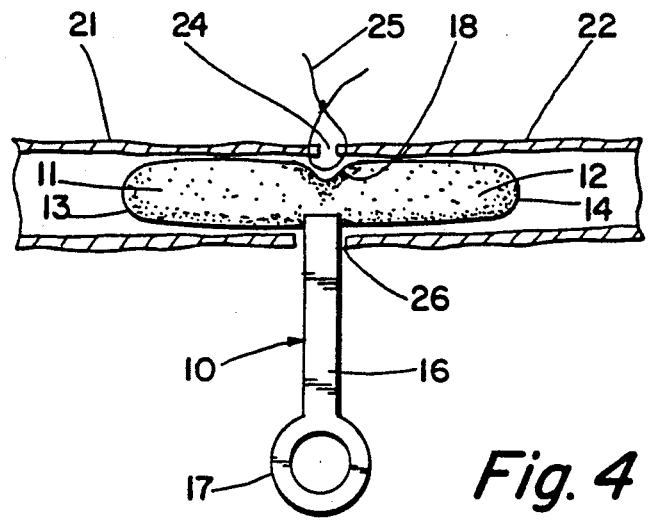
FIG. 4 is a cross-sectional view showing the vessel approximation device of FIG. 1 in place as in FIG. 2.

The vessel segments 21 and 22 are then attached to each other across the gap 24 by placing sutures 25 between the vessel segments. The suturing is started on the side opposite the stem 16, and is continued working toward the stem. No sutures are placed along the side where the stem 16 is located, leaving an opening 26 (FIG. 4, 5) through which the stem extends. This suturing is assisted by the presence of the vessel approximation device 10, since the device prevents the opposite side of the vessel from catching in the sutures which could otherwise result in an occlusion of the vessel. In addition the contrasting color of the vessel approximation device 10 highlights the gap 24 and helps define for the surgeon the line to be sutured.

After this placing of the sutures 25 is accomplished, the sutures 20 which hold the device 10 in place can be removed, and the stem 16 can be used to rotate the vessel segments 21 and 22 to view the opposite side of the vessel segments. Any necessary additional suturing can then be accomplished.

Figure 5:
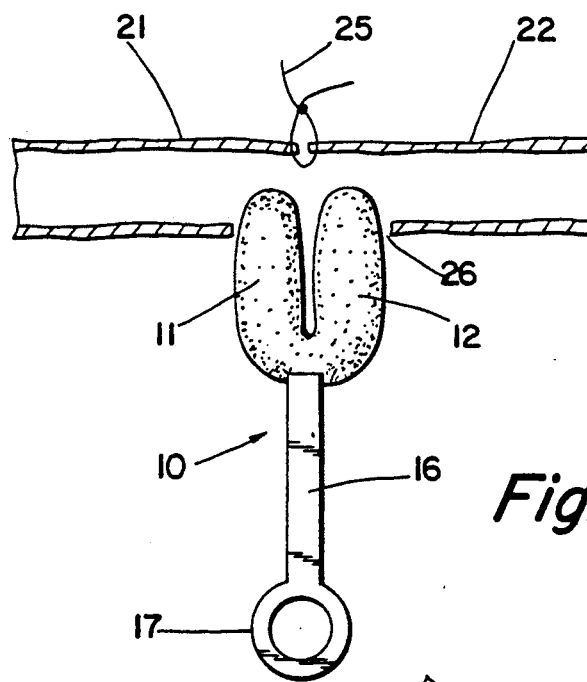
FIG. 5 is a cross-sectional view similar to FIG. 4, showing the vessel approximation device during removal as in FIG. 3.

When all of these sutures are in place, the approximation device 10 can be removed by grasping the stem 16 close to the arms 11 and 12 using a nonserrated pickup or forceps and gently pulling on the stem 16 in the direction perpendicular to the vessel segments 21 and 22 as shown in FIGS. 3 and 5. The two arms 11 and 12 fold inwardly and collapse toward each other through the assistance of the notch 18, allowing the entire vessel approximation device 10 to become essentially linear so that it can be removed through the unsutured opening 26 between the vessel segments 21 and 22 with a minimal amount of trauma.

After the vessel approximation device 10 has been removed, the opening 26 is sutured closed, and the entire anastomosis is inspected. The vessel occluder which was applied to the vessel segments is removed to allow flow across the anastomosis. If there is any leakage, additional sutures may be required. When flow proceeds without leakage, the anastomosis is complete.

Figure 6:
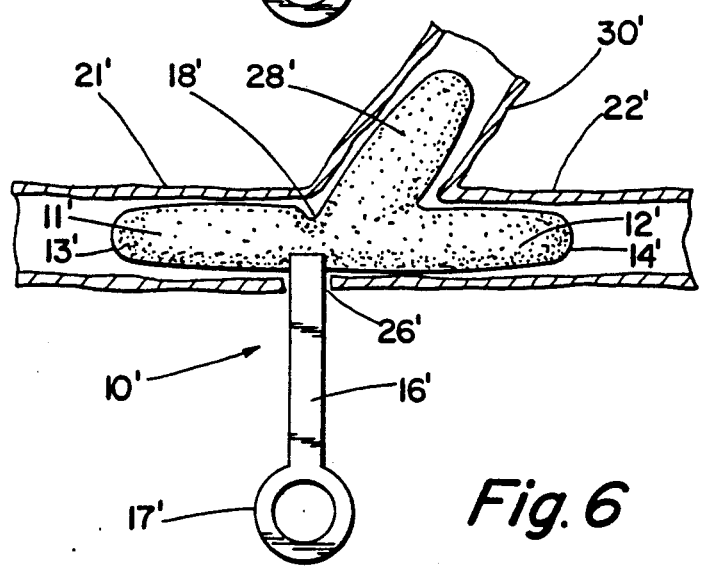
FIG. 6 is a cross-sectional view similar to FIG. 4 showing another embodiment of the vessel approximation device of the present invention.

Various modifications may be made to the vessel approximation device shown in FIGS. 1-5. For example, while the vessel approximation device 10 is shown with two arms 11 and 12 which are generally coaxial so that an angle of approximately 180° is formed between the arms, the arms may be arrange at other angles. One such modification is shown in FIG. 6. The vessel approximation device 10' of FIG. 6 has two arms 11' and 12' which correspond to the arms 11 and 12 of the device 10 previously described, and the device 10' has a third arm 28' which forms an angle of approximately 45° between with one of the arms 12'. As with the device 10 previously described, the vessel approximation device includes tapered tips 13' and 14', a stem 16', a ring 17' and a notch 18'. This vessel approximation device 10' may be used for end-to-site anastomoses with two vessel segments 22' and 30' which would branch from another vessel segment 21'. Thus, any suitable angle may be provided between the arms in order to accommodate the desirable vessel arrangement. The vessel approximation device 10' of FIG. 6 would be used in a manner similar to the vessel approximation device 10 already described.

While the invention has been shown and described with respect to particular embodiments thereof, these are for the purpose of illustration rather than limitation, and other variations and modifications of the specific embodiment herein shown and described will be apparent to those skilled in the art all within the intended spirit and scope of the invention. Accordingly, the patent is not to be limited in scope and effect to the specific embodiments herein shown and described nor in any other way this is inconsistent with the extent to which the progress in the art has been advance by the invention.

What is claimed is:

1. A method of performing vessel anastomosis, comprising the steps of:
    inserting one end of a first vessel segment onto an arm of a generally T-shaped device having two opposed continuous arms meeting at a junction and having a stem extending from the junction of the arms and having a notch at the junction of the arms opposite the stem;
    inserting one end of a second vessel segment onto the other arm of the generally T-shaped device;
    suturing the first and second vessel segments together except along the side that the stem extends from the arms, the side which has not been sutured forming an opening through which the stem extends;
    withdrawing the device through the opening by pulling on the stem and permitting the arms to collapse toward each other at the location of the notch; and
    suturing the opening closed.

2. A method of performing anastomosis as defined in claim 1, comprising the additional step of selecting the generally T-shaped device from a variety of generally T-shaped devices having arms of various sizes such that the arms fit within the vessel segments and support the vessel segments.

3. A method of performing anastomosis as defined in claim 2, wherein the first and second segments are sutured together with the arms of the generally T-shaped device providing a form to support the vessel segments and to prevent the opposite side of each vessel segment from catching in the sutures.

4. A method of performing anastomosis as defined in claim 3, comprising the additional step of suturing the device in place in the surgical field by using suture attachment means on the end of the stem.

5. A method of performing anastomosis as defined in claim 4, wherein the device is sutured in place prior to the steps of inserting the segments onto the arms.

6. A method of performing anastomosis as defined in claim 5, wherein the device is sutured in place using a ring on the end of the stem.

7. A method of performing anastomosis as defined in claim 6, wherein the device is sutured in place using a ring on the end of the stem that is in the same plane as the arms.

8. A method of performing anastomosis as defined in claim 7, wherein the segments are inserted onto a device having two arms by inserting the segments onto a tapered tip of each arm, the tip of each arm being tapered to assist in placing an end of the vessel segment onto the arm.

9. A method of performing anastomosis as defined in claim 8, wherein the device is withdrawn by pulling on a stem that is substantially thinner than the arms to permit the ends of the vessel segments placed over the arms to be proximate to each other to be sutured together.

10. A method of performing anastomosis as defined in claim 9, wherein the segments are inserted onto arms that are colored in contrast to the field to aid in visual location of the device and placement of the sutures.

* * * * *

UNITED STATES PATENT AND TRADEMARK OFFICE
CERTIFICATE OF CORRECTION

PATENT NO. : 5,037,428
DATED : August 6, 1991
INVENTOR(S) : George J. Picha, et al.

It is certified that error appears in the above-identified patent and that said Letters Patent is hereby corrected as shown below:

Column 6, line 26, change "claim 2" to --claim 1--.

Column 6, line 32, change "claim 3" to --claim 1--.

Column 6, line 39, change "claim 5" to --claim 4--.

Column 6, line 46, change "claim 7" to --claim 1--.

Column 6, line 52, change "claim 8" to --claim 1--.

Column 6, line 58, change "claim 9" to --claim 1--.

Signed and Sealed this

Nineteenth Day of January, 1993

Attest:

DOUGLAS B. COMER

*Attesting Officer*　　　*Acting Commissioner of Patents and Trademarks*